US009334177B1

United States Patent
Niell, III et al.

(10) Patent No.: US 9,334,177 B1
(45) Date of Patent: May 10, 2016

(54) CORELESS TRANSFORMER UV LIGHT SOURCE SYSTEM

(71) Applicant: Diversified Technologies, Inc., Bedford, MA (US)

(72) Inventors: Frederick Marvin Niell, III, Lexington, MA (US); Marcel Pierre Joseph Gaudreau, Lexington, MA (US)

(73) Assignee: Diversified Technologies, Inc., Bedford, MA (US)

( * ) Notice: Subject to any disclaimer, the term of this patent is extended or adjusted under 35 U.S.C. 154(b) by 0 days.

(21) Appl. No.: 14/718,577

(22) Filed: May 21, 2015

(51) Int. Cl.
*A61N 5/06* (2006.01)
*C02F 1/32* (2006.01)
*A61L 2/10* (2006.01)
*H05G 2/00* (2006.01)

(52) U.S. Cl.
CPC . *C02F 1/325* (2013.01); *A61L 2/10* (2013.01); *H05G 2/008* (2013.01)

(58) Field of Classification Search
CPC ........... H05G 1/38; H05G 1/52; H05G 2/001; H05G 2/003; H05G 2/005; H05G 2/006; H05G 2/008; H05H 1/0012
USPC .......................................... 250/504 R, 493.1
See application file for complete search history.

(56) References Cited

U.S. PATENT DOCUMENTS

| 5,757,130 | A * | 5/1998 | Dolan | G03F 7/70016 313/345 |
| 2006/0006775 | A1* | 1/2006 | Smith | H05G 2/003 313/31 |
| 2007/0138927 | A1* | 6/2007 | Weger | H01J 65/048 313/231.01 |
| 2008/0142729 | A1* | 6/2008 | Chen | H01J 37/321 250/424 |

* cited by examiner

*Primary Examiner* — Nicole Ippolito
*Assistant Examiner* — Jason McCormack
(74) *Attorney, Agent, or Firm* — Iandiorio Teska & Coleman, LLP

(57) ABSTRACT

A coreless transformer ultra-violet (UV) light source system comprising a bulb including a predetermined amount of an element which efficiently emits UV light when exposed to a high current plasma state and a predetermined amount of a buffer gas therein. An optically thin mesh primary surrounds a portion of the bulb. A pulsed radio frequency (RF) oscillator is coupled to the primary configured to drive high current pulses into the primary causing the light emitting element to form a conducting secondary comprised of the element in a plasma state thereby causing the element to efficiently emit UV light.

22 Claims, 7 Drawing Sheets

CORELESS TRANSFORMER UV LIGHT SOURCE SYSTEM

FIELD OF THE INVENTION

The subject invention relates to a coreless transformer UV light source system.

BACKGROUND OF THE INVENTION

Conventional ultra violet (UV) light sources provide very bright, broadband light which may be useful in a variety of commercial applications, such as UV water disinfection for municipalities and the like, or other applications where UV light is needed.

One typical conventional UV light source or lamp includes a bulb filled with a noble gas or a mixture of noble gases and trace amounts of a light emitting element, such as mercury. A radio frequency (RF) generator is coupled to a primary winding on a magnetic core which surrounds a portion of the bulb. The RF generator provides radio frequency power to the magnetic core wrapped around the lamp. This induces a high current Townsend-type avalanche in the lamp, in turn ionizing the gases in the bulb to form a plasma. The high current in the plasma excites the molecules of the light emitting element or elements, causing them to emit UV light.

One problem with conventional UV lamps is the magnetic coupling core surrounding the bulb, which blocks the UV light. Another problem with conventional UV lamps is that since more power is needed to create more UV light, the size of the transformer increases with the desired light output. As the size of the transformer increases, more light is blocked. This results in large, lossy light blocking magnetic cores. Such cores may require extensive cooling and may put a hard limit on the power transfer to plasma, the optical efficiency, and the radiant light flux. Thus, this is a significant scaling problem when large amounts of UV light is needed, such as for UV water disinfection, polymer curing, ink curing, or other similar applications which require a high brightness UV light source.

BRIEF SUMMARY OF THE INVENTION

This invention features a coreless transformer ultra-violet (UV) light source system comprising a bulb which includes a predetermined amount of an element which efficiently emits UV light when exposed to a high current plasma state and a predetermined amount of a buffer gas therein. An optically thin mesh primary surrounds a portion of the bulb. A pulsed radio frequency (RF) oscillator is coupled to the primary and configured to drive high current pulses into the primary causing the light emitting element to form a conducting secondary comprised of the element in a plasma state thereby causing the element to efficiently emit UV light.

In one embodiment, the light emitting element may include one or more of mercury (Hg), sulfur (S), iodine (I), magnesium (Mg), and others. The buffer gas may include a noble gas. The buffer gas may include one or more of: argon (Ar), neon (Ne), and xenon (Xe). The pulse oscillator may be configured to drive the optically thin mesh primary with average power in the range of about 1.0 kW to about 50 kW. The pulsed oscillator may be configured to drive the high current pulses at a frequency of about 500 kHz and a current in the range of about 1 kA to about 2 kA. The light emitting element in the plasma state may emit UV light having a wavelength in the range of about 110 nm to about 340 nm. The wavelength of the UV light may be configured to kill one or more pathogens. A reflector surrounding a portion of the bulb may be configured to reflect the UV light in a predetermined direction. The bulb may have a toroidal shape. The coreless transformer UV light source may include a pipe surrounded by at least a portion of the bulb configured to receive a flow of fluid. The coreless transformer UV light source may include a reflector to direct the UV light at the flow of fluid to kill one or more pathogens in the flow of fluid. The flow of fluid may include a flow of water. The bulb may be configured to be air cooled when the wavelength of the V light is in the range of about 110 nm to about 170 nm. The bulb may be configured to be liquid cooled when the wavelength of the UV light is in the range of about 180 nm to about 340 nm. The predetermined amount of the element and the predetermined amount of buffer gas may be optimized to efficiently emit said UV light. The gas of the element may include mercury and the buffer gas includes neon. The element may include mercury and the buffer gas includes xenon. The coreless transformer UV light source may include a coating of a mitigation material on an inner surface of the bulb configured to mitigate damage from the element, plasma, and the UV light. The mitigation material may include one or more of ceramic, Yttria ($YO_3$), Alumina ($Al_2O_3$), Ceria (CeO), magnesium (Mg), and barium (Ba). The bulb may be made of fused silica. The optically thin mesh may be made of copper (Cu), tungsten (W), or molybdenum (Mo).

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
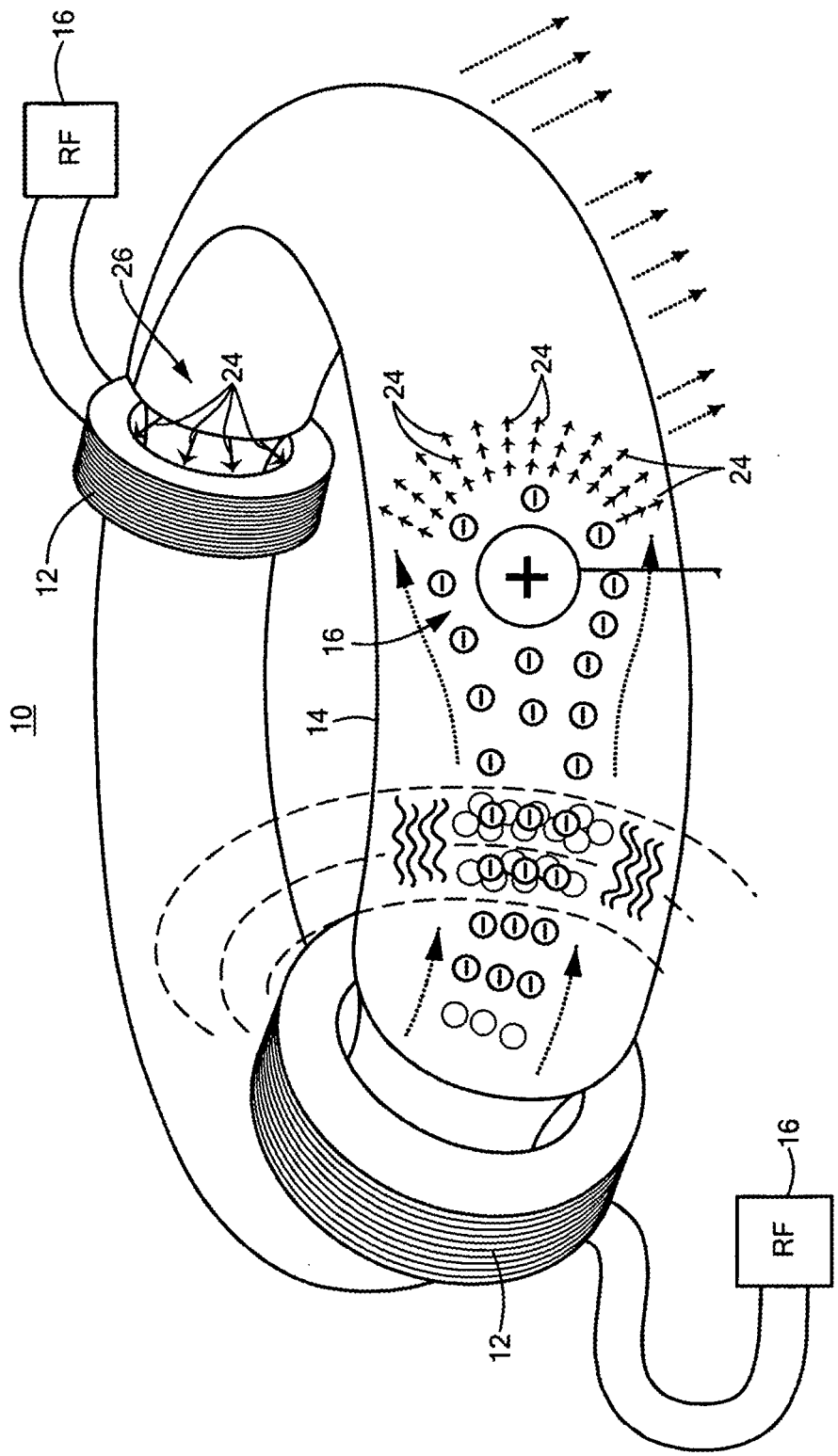
FIG. 1 is a schematic block diagram of one example of a conventional UV light source.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are } not to be read restrictively unless there is clear and convincing evidence manifesting a certain exclusion, restriction, or disclaimer.

As discussed in the Background section above, one conventional UV light source 10, FIG. 1, relies on one or more magnetic primary cores or coils 12 which surround bulb 14. RF source 16 drives primary cores 12 and causes them to induce a high electron current inside bulb 14 which creates a plasma state inside bulb 14. Inside bulb 14 is small amount of a light emitting material in a liquid state or as a solid, such as mercury or similar light emitting material which becomes ionized and interacts with the plasma. Ionized light emitting molecules of the light emitting element in the plasma state, e.g., molecule 16, interact with the electron current, and are excited, thereby generating UV light, exemplarily indicated at 24.

One problem with conventional UV light source 10 is magnetic primary cores 12 block UV light 24 emitted from bulb 14, e.g., as indicated at 26. As discussed in the Background section above, there is also a significant scaling problem when large amounts of UV light is needed, especially in a small compact space. Higher power sources can be built with low temperature plasmas, but require large, lossy, light-blocking magnetic cores. These cores require extensive cooling and may place a hard ceiling on power transfer to the plasma, optical efficiency, and ultimately on radiant light flux. Additionally, when higher power sources are needed, larger magnitude coils 12 are needed which blocks even more light.

Figure 2A:
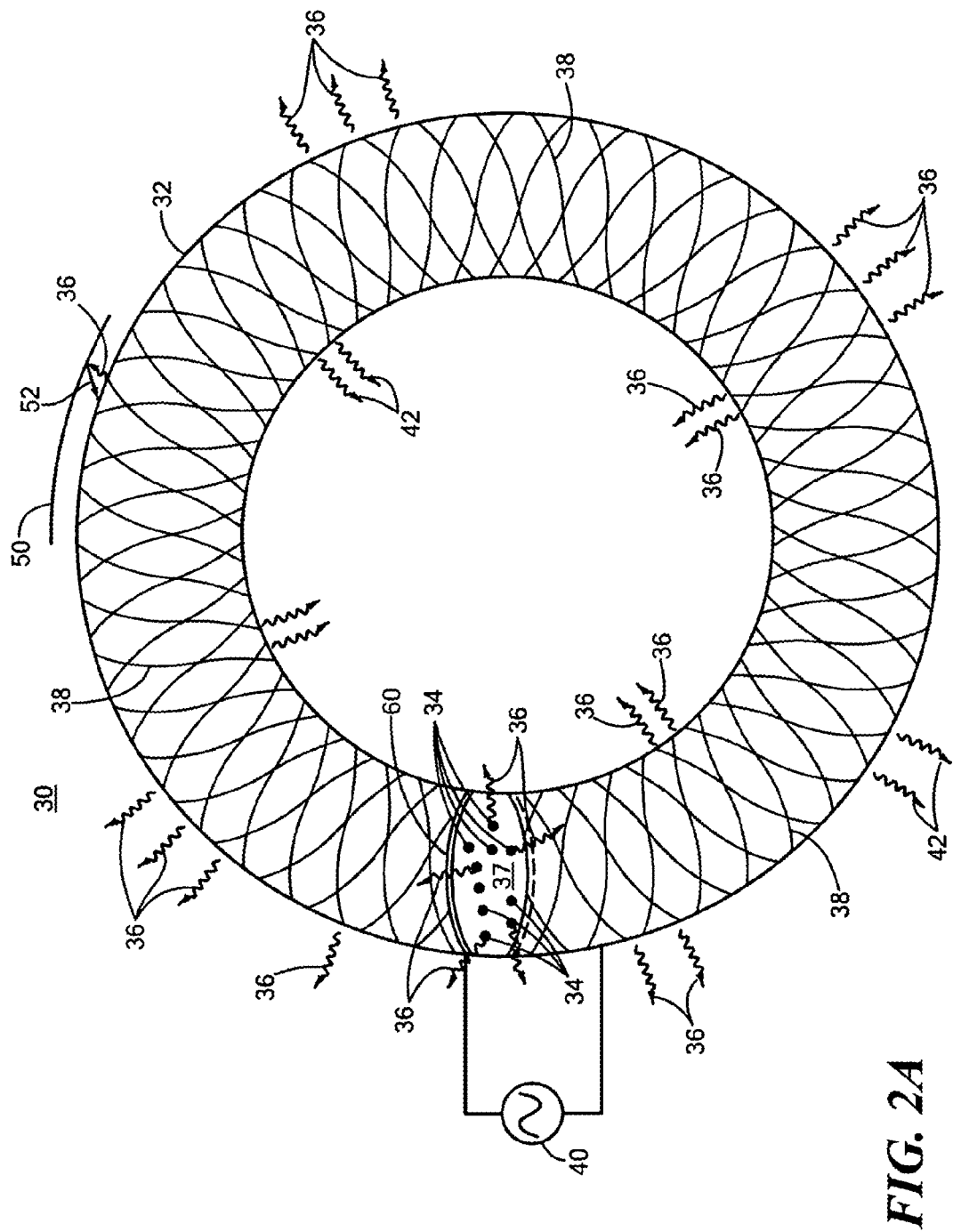
FIGS. 2A-2B is a schematic block diagrams showing the primary components of one embodiment of the coreless transformer UV light source system of one embodiment of this invention.
Figure 2B:
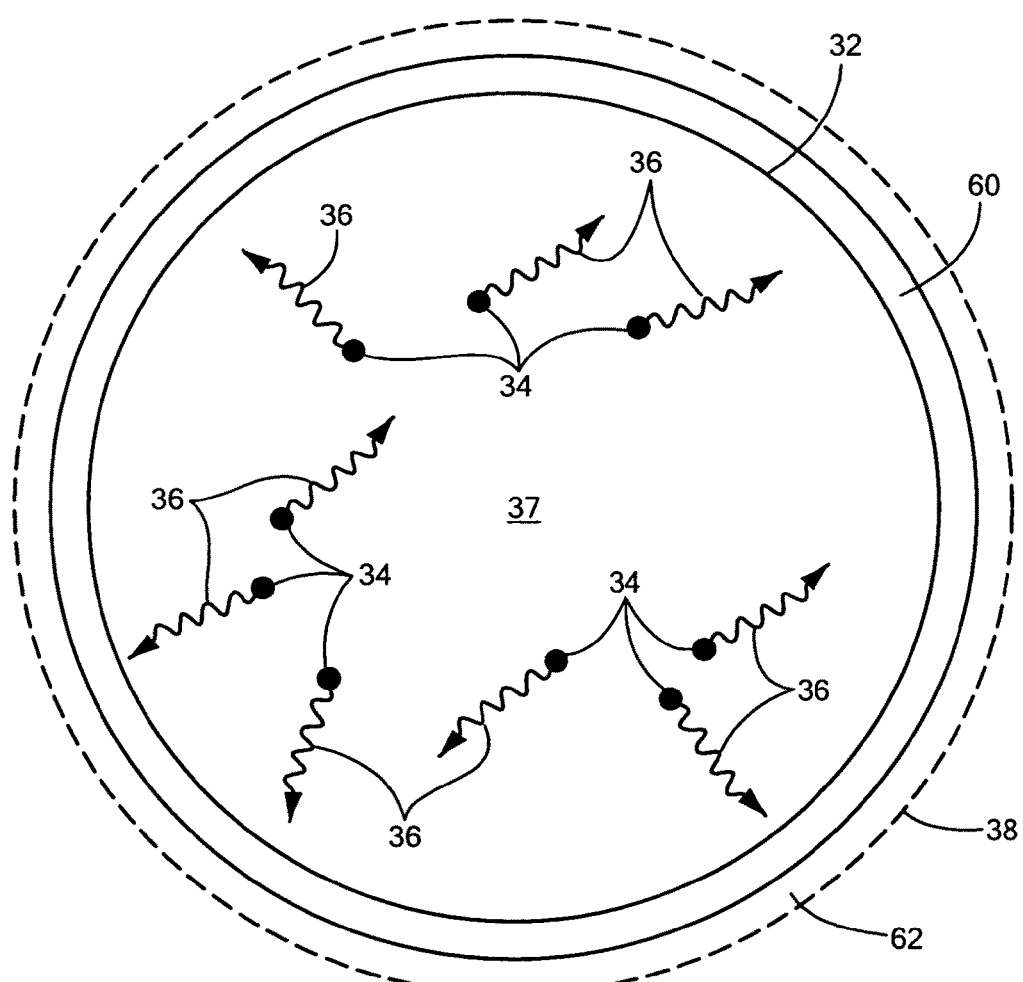

Coreless transformer UV light source system 30, FIG. 2A, of one embodiment of this invention, includes bulb 32 having a predetermined amount element therein, exemplarily indicated at 34, shown in greater detail in FIG. 2B, which efficiently emits UV light 36 when exposed to a high current plasma state. In one example, light emitting element 34 may mercury (Hg), sulfur (S), magnesium, (Mg), iodine (I), or similar type element, in liquid or solid form which vaporizes as it interacts with the plasma, as discussed above. In one design, the predetermined amount of light emitting element 34 may be about 1 mg of liquid Hg for a 7" major diameter, 1" minor diameter bulb 32. Other amounts light emitting element 34 may be used for different sized bulbs, as known by those skilled in the art.

Coreless transformer UV light source system 30 also includes a predetermined amount of buffer gas 37 inside bulb 32. Buffer gas 36 may be a noble gas, such as argon (Ar), neon (Ne), xenon (Xe), or similar noble gas, any combination thereof. In one example, 2 Torr of neon (Ne) buffer gas may be used, or in equally 500 mTorr of argon (Ar).

Coreless transformer UV light source system 30 also includes optically thin mesh primary 38 surrounding a portion of bulb 32 as shown. Although in the example shown, optimally this mesh 38 surrounds all of bulb 32, in other examples, mesh 38 need only surround a portion of bulb 32. In one example, optically thin mesh primary 38 is configured as a high-transparency copper (Cu), tungsten (W), or molybdenum (Mo) or similar material cage on the surface of bulb 32. In one embodiment, optically thin mesh primary 38 may be configured to block only 1% of UV light 36.

Figure 3:
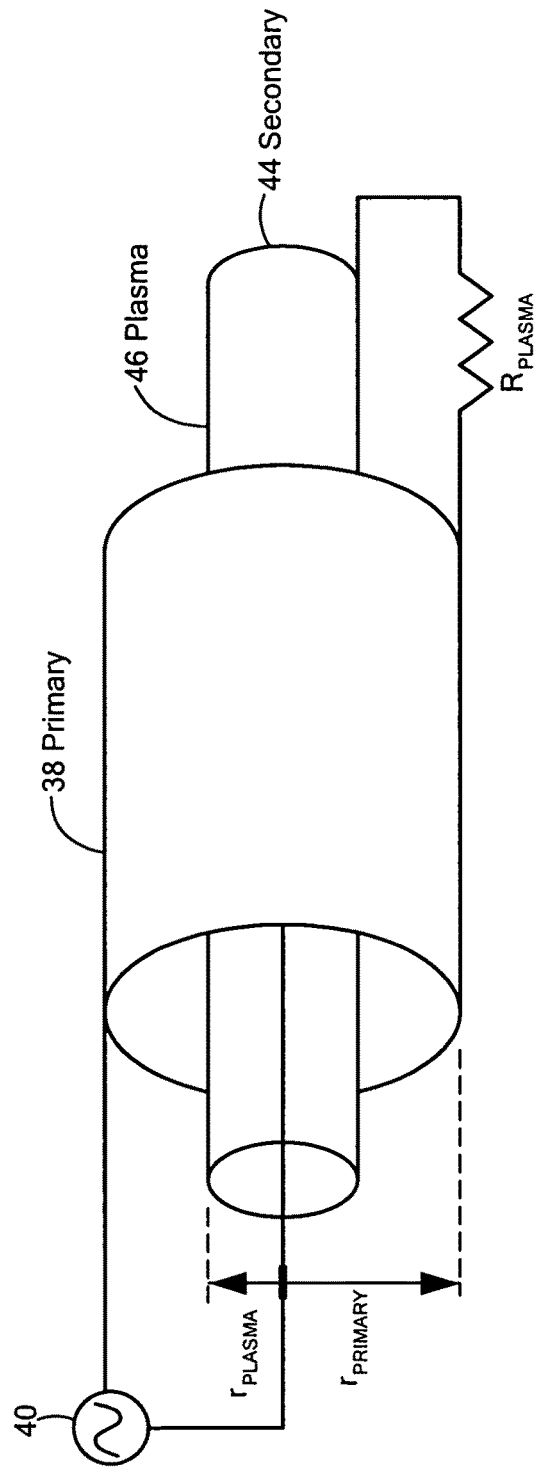
FIG. 3 is a schematic block diagram showing in further detail the structure of the thin mesh primary and the conducting secondary shown in FIGS. 2A-2B.
Figure 4:
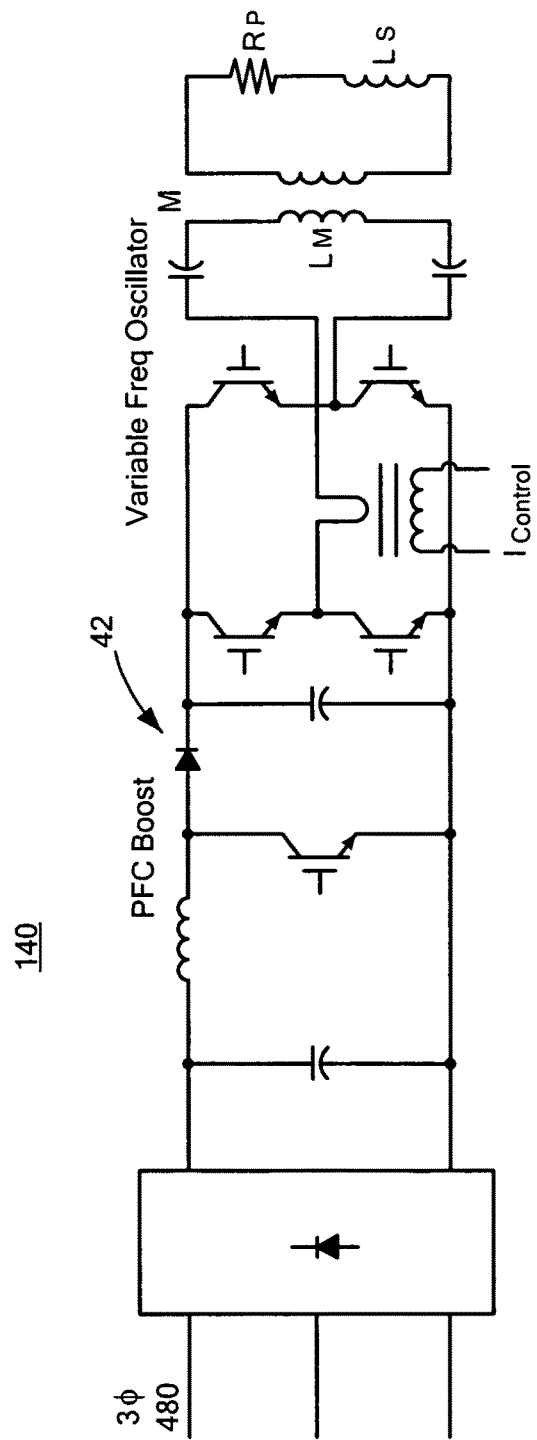
FIG. 4 is a circuit diagram showing one example of the pulse RF oscillator shown in one or more of FIGS. 2-3.

System 30 also includes pulsed radio frequency (RF) oscillator 40 coupled to primary 38 configured to drive high current pulses into primary 38 causing light emitting element 34 to form conducting secondary 44, FIG. 3, comprised of light emitting element 34 in plasma state 46 thereby causing light emitting element 34, FIGS. 2A-2B, to efficiently emit UV light, as exemplarily shown at 36. FIG. 4 shows in further detail, one example of pulsed RF oscillator 40, e.g., an HPRF001, available from Diversified Technologies, Inc., Bedford, Mass. In this example, pulsed RF frequency oscillator 40 includes a power inverter and an LF band oscillator and input circuit 42 as shown. In one example, circuit 42 preferably begins with a conventional boundary-conduction mode power factor correction (PFC) boost converter, taking the input rectified 480 VAC and boosting it to about 800 V. This low boost voltage allows the use of 1200 V insulated gate bipolar transistors (IGBTs) in the full bridge that follows. The H-bridge circuitry shown alternately discharges and recharges the capacitors on each zero-current switching (ZCS) cycle. In one example, RF oscillator is configured to drive primary 38 with an average power in the range of about 1.0 kW to about 50 kW. RF oscillator may also be configured to drive high current pulses at a frequency of about 500 KHz and a current in the range of about 1 KA to about 2 KA. In one example, RF oscillator 40 may provide a pulsed high-power discharge, e.g., 0.5 $MW_{pk}$, 500 kHz, less than about 5% of the duty cycle, which creates short-duration high plasma temperatures while maintaining a much lower steady-state temperature. This enables shorter wavelength emission of UV light 36.

The result is coreless transformer UV light source system 30, FIGS. 2A-4, with optically thin mesh primary 38 efficiently and effectively emits almost all of UV light 36 created without the need for light blocking magnetic primary cores found in typical conventional UV light systems. System 30 also eliminates the problems associated with large, lossy, light-blocking magnetic cores found in conventional UV light sources when large amounts of UV light are needed. System 30 also eliminates the hard ceiling on power transfer to the plasma and improves optical efficiency. Additionally, the pulsed high power discharge provided by RF oscillator 40 creates short duration high plasma temperatures while maintaining a much lower steady state temperature. This enables shorter wavelength emission of UV light that would be impossible for a similarly powered continuous conventional discharge lamp. In one example, system 30 can provide about a 50 kW electrical input which far exceeds conventional electrode mercury lamp systems. Thus, system 30 can be scaled to large commercial applications, such as for use with water disinfection for municipalities, large-scale polymer crosslinking and curing, ink curing, and similar applications which require a high brightness UV light source.

In one example, UV light 36 output by system 30 has a wavelength in the range of about 110 nm to about 340 nm. Preferably, the wavelength of light 42 is configured to kill one or more pathogens such as bacteria, viruses, or other microorganisms that can cause disease.

System 30, FIG. 2A, may also include reflector 50 surrounding a portion of bulb 32 configured to reflect UV light 36 in a predetermined direction, e.g., as shown at 52. In one embodiment, bulb 32 preferably has a toroidal shape as shown in FIG. 2A.

Preferably, optically thin mesh primary 38 is spaced the bulb 32, e.g. as indicated at 62, FIG. 2B, to prevent migration of primary mesh metals into bulb surface 32 at high temperatures.

In one design, bulb 32 is configured to be air cooled when the wavelength of UV light 36 is in the range of about 110 nm to about 170 nm. In another example, bulb 32 is configured to be liquid cooled when the wavelength of UV light 36 is in the range of about 180 nm to about 340 nm.

Figure 5:
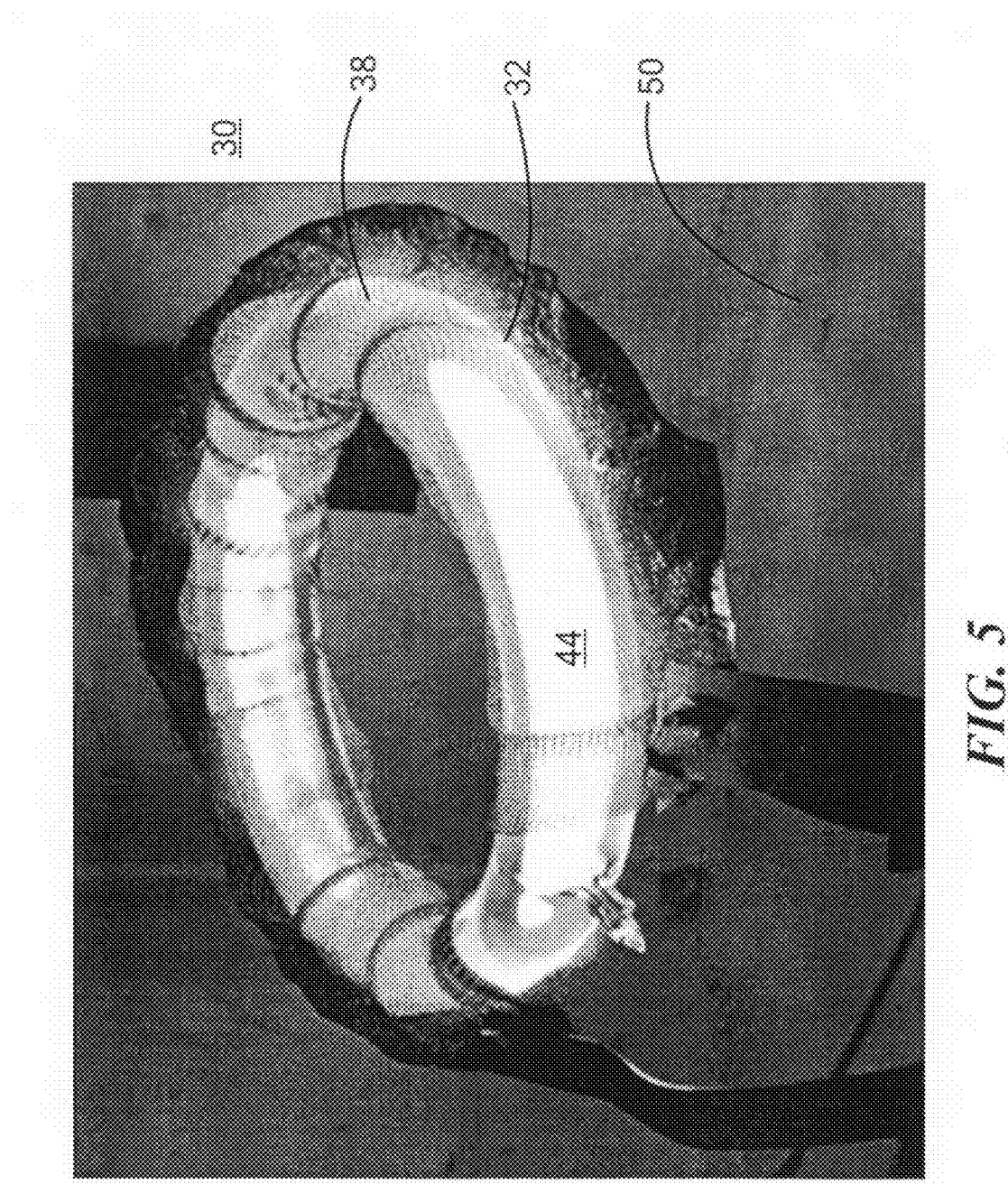
FIG. 5 is a photograph showing one example of the coreless transformer UV light source system shown in one or more of FIGS. 2A-3 immersed in water.

FIG. 5, where like parts include like numbers, shows one example of coreless transformer UV light source system 30 with bulb 32, and primary mesh 38, and plasma 44, shown here as illuminated, being cooled in water 50.

Preferably, the predetermined amount of light emitting element 34 and the predetermined amount of gas 35 is optimized to efficiently emit UV light 36. In one example, the air-cooled bulb was optimized to have a major diameter of 8" and a minor diameter of 1.5" and filled with 2 Torr of xenon (Xe) and 1 mg of mercury (Hg). In another water-cooled example, the light emitting element 34 may be 100 mg mercury (Hg) and buffer gas 36 may be 10 Torr neon (Ne). In another example, light emitting element 34 may be sulfur (S) and buffer gas 36 may be argon (Ar).

In one design, bulb 32, FIG. 2A, may include coating 60, shown in greater detail in FIG. 2B, of a mitigation material on the inner surface of bulb 32 as shown configured to mitigate damage from the plasma, the light emitting element 34, and UV light 36. In one example, the mitigation material includes various coatings, including but not limited to Yttria ($YO_3$), Alumina ($Al_2O_3$), Ceria (CeO), and the like. Other mitigation materials may include magnesium (Mg) or barium (Ba) metal to scavenge free radical oxygen from inside the bulb plasma to prevent mercuric (or mercurous) oxides film formation inside the bulb. In one design, bulb 32, FIGS. 2A-5 may be made of fused silica.

Figure 6:
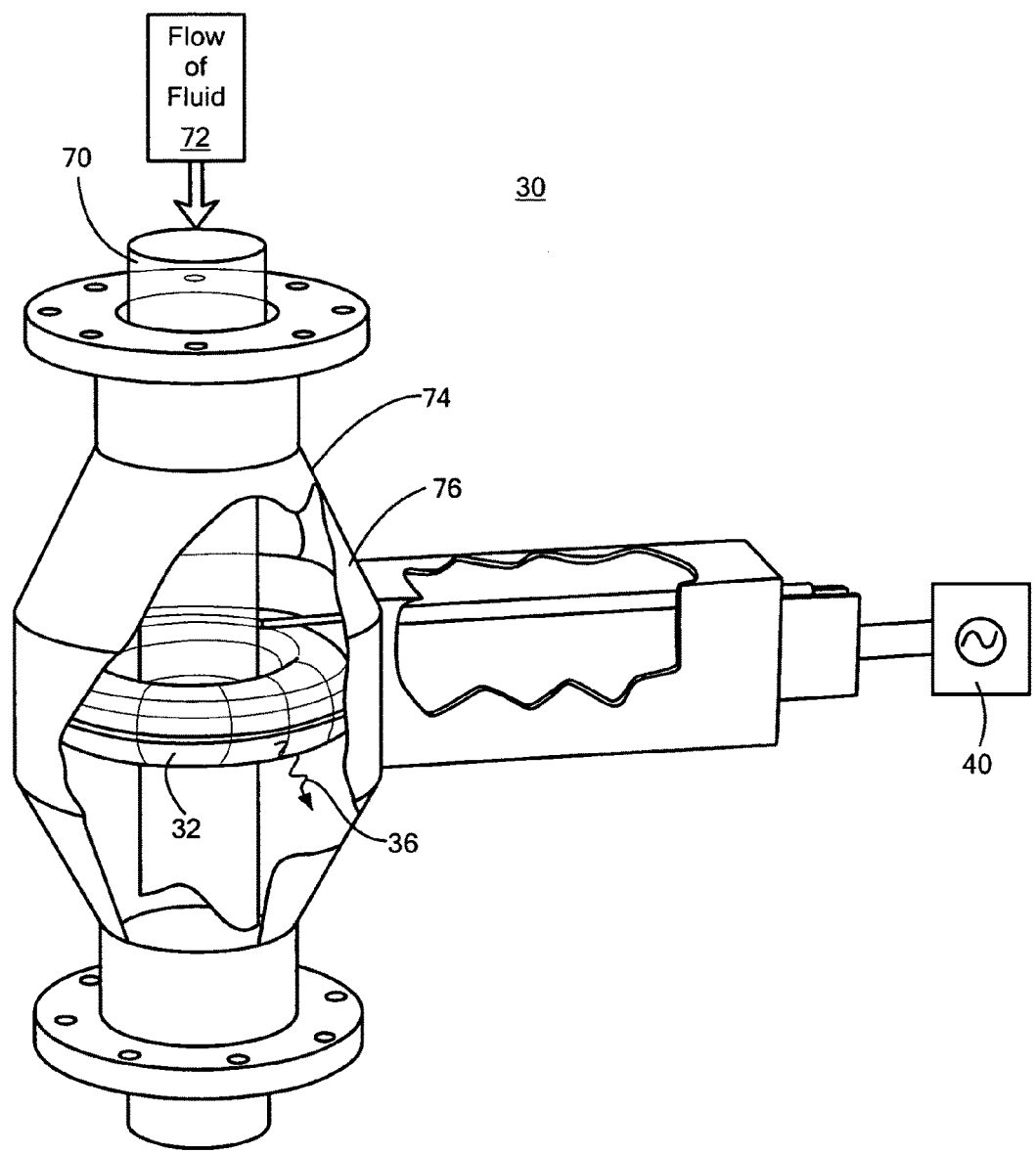
FIG. 6 is a schematic block diagram of another embodiment of the coreless transformer UV light source system of this invention.

Coreless transformer UV light source system 30', FIG. 6, where like parts have been given like numbers, preferably includes pipe 70 configured to receive flow of fluid 72. System 30' also preferably includes reflector 74 configured to direct UV light 36 to flow of fluid 72 in pipe 70. In this example, UV light 36 directed to flow of fluid 72 in pipe 70 preferably to kills one or more pathogens in flow of fluid 72. Flow of fluid 72 may be drinking water from a municipality or other similar water source. Because coreless transformer UV light source system 30 does not require a magnetic primary, system 30 can be scaled commercial applications efficiently and effective disinfect and denature waste water. The light source can also effectively be scaled to any chemical process requiring large-scale catalysis, polymerization, or other UV curing in liquid or other product where intense, high brightness UV light sources are required.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A coreless transformer ultra-violet (UV) light source system comprising:

a bulb including a predetermined amount of an element which efficiently emits UV light when exposed to a high current plasma state and a predetermined amount of a buffer gas therein;
an optically thin mesh primary surrounding a portion of the bulb; and
a pulsed radio frequency (RF) oscillator coupled to the primary configured to drive high current pulses into the primary causing the light emitting element to form a conducting secondary comprised of the element in a plasma state thereby causing the element to efficiently emit UV light.

2. The system of claim 1 in which the light emitting element includes one or more of mercury (Hg), sulfur (S), magnesium (Mg), iodine (I), and others.

3. The system of claim 1 in which the buffer gas includes a noble gas.

4. The system of claim 3 in which the buffer gas includes one or more of: argon (Ar), neon (Ne), and xenon (Xe).

5. The system of claim 1 in which the pulse oscillator is configured to drive the optically thin mesh primary with an average power in the range of about 1.0 kW to 50 kW.

6. The coreless transformer UV light source of claim 1 in which the pulsed oscillator is configured to drive the high current pulses at a frequency of about 500 kHz and a current in the range of about 1 kA to about 2 kA.

7. The coreless transformer UV light source of claim 1 in which the light emitting element in the plasma state emits UV light having a wavelength in the range of about 110 nm to about 340 nm.

8. The careless transformer UV light source of claim 7 in which the wavelength of the UV light is configured to kill one or more pathogens.

9. The coreless transformer UV light source of claim 1 further including a reflector surrounding a portion of the bulb configured to reflect the UV light in a predetermined direction.

10. The coreless transformer UV light source of claim 1 in which the bulb has a toroidal shape.

11. The coreless transformer UV light source of claim 1 further including a pipe surrounded by at least a portion of the bulb configured to receive a flow of fluid.

12. The coreless transformer UV light source of claim 11 further including a reflector to direct the UV light at the flow of fluid to kill one or more pathogens in the flow of fluid.

13. The system of claim 12 in which the flow of fluid includes a flow of water.

14. The coreless transformer UV light source of claim 7 in which the bulb is configured to be air cooled when the wavelength of the V light is in the range of about 110 nm to about 170 nm.

15. The coreless transformer UV light source of claim 7 in which the bulb is configured to be liquid cooled when the wavelength of the UV light is in the range of about 180 nm to about 340 nm.

16. The coreless transformer UV light source of claim 1 in which the predetermined amount of the element and the predetermined amount of buffer gas is optimized to efficiently emit said UV light.

17. The coreless transformer UV light source of claim 16 in which the gas of the element includes mercury and the buffer gas includes neon.

18. The coreless transformer UV light source of claim 16 in which the element includes mercury and the buffer gas includes xenon.

19. The careless transformer UV light source of claim 1 further including a coating of a mitigation material on an inner surface of the bulb configured to mitigate damage from the element, plasma, and the UV light.

20. The coreless transformer UV light source of claim 19 in which the mitigation material includes one or more of ceramic, Yttria ($YO_3$), Alumina ($Al_2O_3$), Ceria (CeO), magnesium (Mg), and barium (Ba).

21. The coreless transformer UV light source of claim 1 in which the bulb is made of fused silica.

22. The coreless transformer UV light source of claim 1 in which the optically thin mesh is made of copper (Cu), tungsten (W), or molybdenum (Mo).

\* \* \* \* \*